United States Patent [19]

Yoshida et al.

[11] Patent Number: 4,608,358
[45] Date of Patent: Aug. 26, 1986

[54] CATALYST FOR THE ISOMERIZATION REACTION OF QUADRICYCLANES TO NORBORNADIENES

[75] Inventors: Zenichi Yoshida; Sadao Miki, both of Kyoto, Japan

[73] Assignee: Sumitomo Chemical Company, Limited, Osaka, Japan

[21] Appl. No.: 680,530

[22] Filed: Dec. 11, 1984

Related U.S. Application Data

[62] Division of Ser. No. 580,262, Feb. 15, 1984, abandoned.

[30] Foreign Application Priority Data

Mar. 9, 1983 [JP] Japan ................................. 58-39799
Mar. 9, 1983 [JP] Japan ................................. 58-39800

[51] Int. Cl.[4] .................. B01J 21/08; B01J 21/04; B01J 21/16; B01J 23/76
[52] U.S. Cl. .................................. 502/164; 502/163; 502/167; 558/383; 560/128; 570/151; 585/353
[58] Field of Search .................. 260/464; 570/151; 585/353; 560/128; 502/163, 164, 167

[56] References Cited

U.S. PATENT DOCUMENTS

| | | | |
|---|---|---|---|
| 2,988,500 | 6/1961 | Gleim et al. | 502/163 X |
| 4,271,038 | 6/1981 | Pesa et al. | 502/163 X |
| 4,276,194 | 6/1981 | Carlson | 502/163 |
| 4,293,442 | 10/1981 | Frame | 502/163 |
| 4,318,825 | 3/1982 | Frame | 502/163 |
| 4,320,029 | 3/1982 | Frame | 502/163 |
| 4,364,843 | 12/1982 | Carlson | 502/163 |

OTHER PUBLICATIONS

King, et al.; J. Org. Chem., 44, (1979), pp. 385-391.

Primary Examiner—Joseph Paul Brust
Attorney, Agent, or Firm—Stevens, Davis, Miller & Mosher

[57] ABSTRACT

The present invention relates to a catalyst for the isomerization reaction from quadricyclanes to norbornadienes in a conversion system from light energy to heat energy which comprises cyclopropenylidene palladium complex represented by the formula,

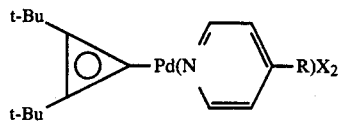

wherein R represents hydrogen atom, a lower alkyl or cyano group and X represents a halogen atom, and further relates to a fixed catalyst for the isomerization reaction from quadricyclanes to norbornadienes in a conversion system from light energy to heat energy which is obtained by adsorption-fixing a porphyrin Co(II) complex represented by the formula,

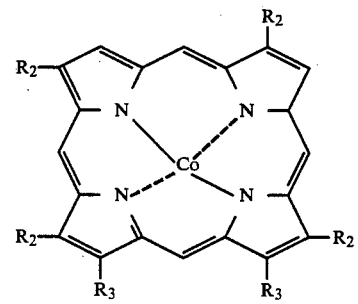

wherein $R_2$ represents a lower alkyl group and $R_3$ represents a hydroxycarbonyl lower alkyl group, to a modified inorganic carrier in which a polyamine sulfone comprising a recurring unit represented by the formula,

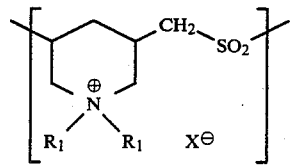

wherein $R_1$ represents a lower alkyl group and X represents a halogen atom, has been adsorbed on a solid inorganic carrier.

1 Claim, No Drawings

CATALYST FOR THE ISOMERIZATION REACTION OF QUADRICYCLANES TO NORBORNADIENES

This is a division of application Ser. No. 580,262, filed Feb. 15, 1984, now abandoned.

The present invention relates to a useful catalyst for the isomerization reaction of quadricyclanes to norbornadienes.

In the so-called conversion system of light energy to heat energy in which norbornadienes such as norbornadiene and its derivatives are isomerized into the corresponding quadricyclanes by irradiation with light (first isomerization), the resulting quadricyclanes can be converted back to the original norbornadienes by isomerization in the presence of a catalyst (second isomerization), and heat generated in the second isomerization is removed, as disclosed in Japanese Patent Application Kokai (Laid-Open) Nos. 147,577/1982 and 149,251/1982, "Kagaku to Seibutsu", Vol. 19, No. 2, 80–88.

To operate this light energy conversion system with good efficiency, the following should be taken into account: In the second isomerization for returning quadricyclanes, to the original norbornadienes, it is desired that the catalyst used in said reaction is supported on and fixed to a solid inert carrier to prevent pollution of the reaction system. It is very important that the reaction yield is high and that the reaction rate also be high. In addition to this, this conversion system is generally operated in a closed and circulating system, so that there is little reduction in the catalytic activity, and that repeated use with good efficiency is possible.

The conventionally well known catalyst used in this isomerization reaction (hereinafter, isomerization simply referred to means the foregoing second isomerization) includes Pd(II) complexes such as Pd(CH$_3$CN)$_2$Cl$_2$,

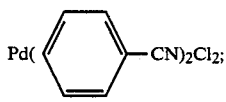

etc. These Pd(II) complexes, however, have a problem in that the reaction rate is slow. A fixed catalyst which has been used in this isomerization reaction, is tetraphenylporphyrin Co (II) [hereinafter, abbreviated to TPPCo (II)] supported on polystyrene [J. Org. Chem., Vol. 44, No. 3, 385–391]. This TPPCo (II)-polystyrene catalyst, however, has a problem in that not only is the reaction yield low but the reaction rate is low, and repeated use of the catalyst causes a marked reduction in the catalytic activity.

For this reason, the present inventors extensively studied to develop Pd (II) complex type catalysts which act to accelerate the reaction rate in the isomerization reaction and also studied fixed catalysts for the reaction which would eliminate various defects inherent in the prior art catalysts, and as a result, obtained the present improved invention.

An object of the present invention is to provide a catalyst for the isomerization reaction from quadricyclanes to norbornadienes characterized in that said catalyst comprises cyclopropenylidene palladium complex represented by the formula (I),

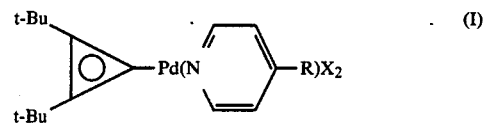

wherein R represents a hydrogen atom, a lower alkyl or cyano group and X represents a halogen atom.

Another object of the present invention is to provide a fixed catalyst for the isomerization reaction from quadricyclanes to norbornadienes obtained by adsorption-fixing a porphyrin Co (II) complex [hereinafter, abbreviated to DP IX Co (II)] represented by the formula (III),

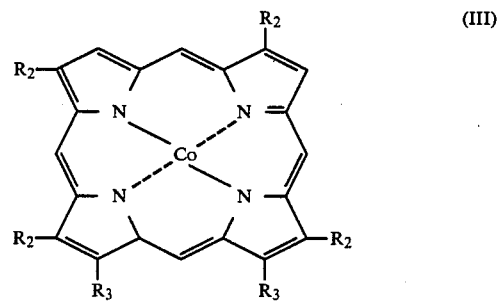

wherein R$_2$ represents a lower alkyl group and R$_3$ represents a hydroxycarbonyl lower alkyl group, to a modified inorganic carrier in which a polyamine sulfone comprising a repeating unit represented by the formula (II),

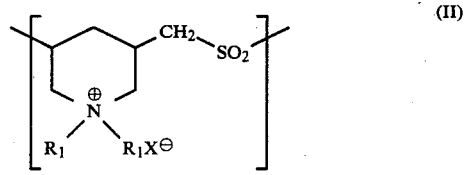

wherein R$_1$ represents a lower alkyl group and X represents a halogen atom, has been adsorbed on a solid inorganic carrier selected from activated alumina, silica gel and kaolin.

Next, the present invention will be illustrated in detail.

The term "quadricyclanes", is meant to relate to various quadricyclane derivatives which include, in addition to quadricyclane having no substituent represented by the formula,

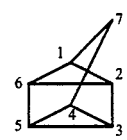

those of which part or all of the 1 to 7 positions have been substituted with one or more members selected from the group consisting of —CH$_3$, —COOCH$_3$,

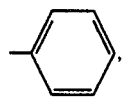

—CN, —CF$_3$ and the like.

The cyclopropenylidene palladium complexes of the present invention are represented by the above formula (I). In this formula, a substituent R is a lower alkyl (e.g. methyl, ethyl, propyl), or cyano group, and a substituent X is chlorine or bromine, but the most preferred R and X are —CN and chlorine, respectively.

This cyclopropenylidene palladium complex can be produced, for example, by refluxing 3,3-dichloro-1,2-di-tert-butylcyclopropene and palladium black in a solvent (e.g. benzene) in an inert gas stream to obtain di-μ-chloro-di-chloro-bis(di-tert-butylcyclopropenylidene)-dipalladium which is then reacted with pyridine or 4-substituted pyridine in a solvent such as dichloromethane. Said complex has a characteristic that it can be successfully isolated although it belongs to a Pd LL' X$_2$-type mixed ligand complex which is generally difficult to isolate because of disproportionation reaction, and also because the cyclopropenylidene group is not liberated from the metal.

In applying the cyclopropenylidene complex of the present invention to the isomerization reaction of quadricyclanes, cyclopropenylidene palladium complex is used in solution with halogenated hydrocarbons such as chloroform, dichloromethane, etc., and its concentration is properly determined according to the conditions of use, being not particularly limited. Low concentrations, however, delay the progress of the isomerization reaction so that use of low concentrations are not practical. The concentration is therefore not less than 0.5 mole % in general.

Quadricyclanes are used in a non-polar solvent solution (e.g. benzene, toluene, pentane, hexane, heptane) having a proper concentration. The amount of the catalyst used is generally 0.001 to 0.5 mole per mole of quadricyclanes, but it may exceed this range depending upon reaction conditions such as reaction temperature, reaction form and the like.

By using the cyclopropenylidene palladium complex of the present invention as a catalyst for the isomerization reaction, the reaction rate becomes very much faster as compared with the use of other palladium complex catalysts. The catalyst of this invention makes the isomerization reaction of quadricyclanes very advantageous in practical use.

The solid inorganic carrier used in the present invention are ones which are commonly used as catalyst-supporting carriers. They include for example activated alumina, silica gel, kaolin and the like, of which activated alumina is preferred. The form of this inorganic carrier may be any powder, granule or the like, and is selected according to the condition of use. Generally, however, granules are more preferably used over powders in terms of pressure loss on the use of catalyst, and the like.

In the polyamine sulfone comprising a repeating unit represented by the formula (II), the substituent R$_1$ is a lower alkyl group such as methyl, ethyl, propyl, etc., and the substituent X is a halogen atom such as chlorine, bromine or iodine. In terms of performance, polyamine sulfone in which X is bromine or iodine is more superior to one in which X is chlorine, but chlorine is advantageous economically and practically.

The polyamine sulfone compounds which are used in the invention are those which are already on the market, for example PAS-A (a product of Nittobo Co.) and the like.

Porphyrin Co(II) complex represented by the formula (III) is synthesized, for example, from protohemin. In said formula, R$_2$ is a lower alkyl group such as methyl, ethyl, propyl, etc., and R$_3$ is a hydroxycarbonyl lower alkyl group such as hydroxycarbonylmethyl, hydroxycarbonylpropyl, hydroxycarbonylbutyl, etc.

The fixed catalyst of the present invention is obtained by adsorption-fixing porphyrin Co(II) complex to a modified inorganic carrier through an ionic bond, said carrier comprising a solid inorganic carrier selected from the group consisting of activated alumina, silica gel and kaolin having polyamine sulfone adsorbed thereon. Specifically, the fixed catalyst can be prepared by dipping the modified inorganic carrier in an organic solvent solution, for example pyridine solution of porphyrin Co(II) complex generally at room temperature for 0.5 to 50 hours, and thereafter removing the solvent.

The concentration of porphyrin Co(II) complex in the organic solvent solution varies with the amount of porphyrin Co(II) to be supported on the carrier, and it may properly be changed according to the condition of use as catalyst. This amount supported is closely related also to the catalytic activity, and the more the amount, the higher the catalytic activity. Generally, however, the amount of porphyrin Co(II) complex is 0.01 to 50 mg per gram of the modified inorganic carrier.

The modified inorganic carrier used above can be obtained, for example, by dipping an inorganic carrier in an aqueous high-concentration solution, preferably an aqueous saturated solution of the polyamine sulfone at room temperature or with heating to impregnate the carrier with the solution, and thereafter, drying the impregnated carrier at 60° to 150° C., preferably 90° to 110° C. for 10 to 100 hours.

For applying the fixed catalyst of the present invention to the isomerization reaction of quadricyclanes to norbornadienes, isomerization is carried out by bringing a non-polar solvent solution (e.g. benzene, toluene, pentane, hexane, heptane, chloroform, carbon tetrachloride, carbon disulfide) of quadricyclanes of a proper concentration into contact with the catalyst of the present invention.

In this reaction, the amount of the fixed catalyst used is generally $1 \times 10^{-6}$ to $1 \times 10^{-3}$ mole, as converted to the amount of Co(II) in porphyrin Co(II) complex, per mole of quadricyclanes. But, the amount may exceed this range according to reaction conditions such as the form, temperature, etc. of the reaction.

The fixed catalyst of the present invention has very superior characteristics never found in the well-known fixed catalysts as described above. It maintains not only a high conversion of the isomerization reaction, but maintains a high-level of catalytic activity through repeated use; and its catalytic activity is restored nearly 100% by heat-treatment at 200° to 300° C. so that its regeneration and re-use become possible. Consequently, the isomerization reaction can be carried out advantageously by using said catalyst.

Next, the present invention will be illustrated with reference to the following examples.

CATALYST PREPARATION EXAMPLE 1

A mixture of 3,3-dichloro-1,2-tert-butylcyclopropene and palladium black in a slight excess thereof was refluxed with benzene in an argon gas stream. After completion of the reaction, the reaction mixture was cooled to room temperature and filtered to obtain a crystal.

To this crystal was added 4-cyanopyridine, and the mixture was stirred in dichloromethane for 10 hours and then filtered to collect the crystal. This crystal was taken as Cat.-A.

In the same manner as above, catalysts were obtained by using pyridine and 4-methylpyridine, respectively, in place of 4-cyanopyridine.

The catalysts obtained were taken as Cat.-B and Cat.-C, respectively.

EXAMPLE 1

0.1 Mole of quadricyclane was isomerized at 30° C. in chloroform containing $5 \times 10^{-1}$ mole of each catalyst, and a period of time required for converting 50% of quadricyclane, to norbornadiene (half-life period) was measured. As a result, the result shown in Table 1 were obtained.

TABLE 1

| Catalyst | Cat.-A | Cat.-B | Cat.-C |
| --- | --- | --- | --- |
| Half-life period | 4.3 min. | 19.1 min. | 21 min. |

CATALYST PREPARATION EXAMPLE 2

Polyamine sulfone (PAS-A, a product of Nittobo Co.) of the formula (II) in which $R_1$ is $CH_3$ and X is Cl, was dissolved in water at room temperature to obtain a saturated aqueous solution. To this solution was added spherical activated alumina (KHA, produced by Sumitomo Aluminum Refining Co.; particle diameter, 4 to 6 mm) at room temperature and after 15 hours dipping, the alumina was heat-dried at 100° C. for 48 hours to obtain modified alumina.

After this modified alumina was dipped for 24 hours in a thoroughly deaerated pyridine solution of porphyrin Co(II) complex of the formula (III) in which substituent $R_2$ is $CH_3$ and substituent $R_3$ is $CH_2CH_2COOH$, the pyridine was removed under reduced pressure to obtain a fixed catalyst having $1.9 \times 10^{-5}$ mole of fixed porphyrin Co(II) complex per gram of the modified alumina.

EXAMPLE 2

A benzene solution of 2,3-dicyano-1,5,6-trimethyl-quadricyclane (hereinafter, abbreviated to Q) was brought into contact with a dichloromethane solution of each catalyst shown in Table 2 at 30° C. for 12 hours with stirring in a flask to isomerize Q into the corresponding norbornadiene (hereinafter, abbreviated to N). As a result, the rate of isomerization of Q→N with each catalyst was shown in Table 2.

Hereupon, the amount of each catalyst used was 0.3 time by mole based on Q, and the catalyst of the present invention was used as solid without using a solvent.

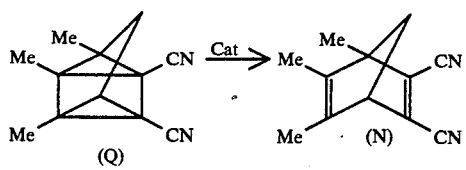

TABLE 2

| No. | Catalyst | Rate of isomerization of Q→N (%) |
| --- | --- | --- |
| Present example | | |
| 1 | Porphyrin Co (II) Complex | 100 |
| Comparative example | | |
| 1 | TPP Co (II) | 18.6 |
| 2 | 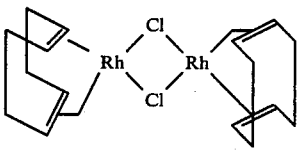 | 3 |
| 3 | AgBF$_4$ | 52.1 |

EXAMPLE 3

Ten millileters of a pentane solution containing 0.1 mole of quadricyclane dissolved was isomerized using $3.1 \times 10^{-6}$ mole, as converted to the amount of Co(II) in porphyrin Co(II) complex, of the fixed catalyst prepared in the catalyst preparation example, and a period of time required for 50% of the quadricyclane to be converted to norbornadiene (half-life period) was measured. As a result, it was found that the half-life period was 18.0 minutes. Further, this isomerization reaction was carried out over and over under the same condition as above except that the catalyst was used repeatedly, and the half-life period was measured at each repeated use of the catalyst. As a result, it was found that the half-life period at the 8th repeated use was 32.1 minutes, which means that the catalytic activity of the 8th repeated use was 56% ($18.0/32.1 \times 100\%$) of that at the 1st use.

For comparison, the isomerization reaction was repeated in completely the same manner as above using TPPCo(II) supported on polystyrene as a catalyst. As a result, it was found that the half-life period at the 1st use of the catalyst was 44.6 minutes and that at the 6th repeated use the half life period long as 88.2 minutes. This means that the catalytic activities at the 1st use and 6th repeated use in this comparative example were 40% and only 20%, respectively, of the catalytic activity of the 1st use, as taken as a standard, of the catalyst of the present invention.

The above test results are shown in Table 3.

TABLE 3

| Number of repetitions | Example Catalyst: Perphyrin Co(II) Complex activated alumina Catalytic activity | | Comparative example Catalyst: TPPCo(II)-polystyrene Catalytic activity | |
|---|---|---|---|---|
| | Half-life period (min) | Activity ratio | Half-life period (min) | Activity ratio |
| 1 | 18.0 | 1 | 44.6 | 0.40 |
| 2 | 19.4 | 0.98 | 62.8 | 0.29 |
| 3 | 20.1 | 0.89 | 80.2 | 0.22 |
| 4 | 26.2 | 0.68 | 89.6 | 0.20 |
| 5 | 25.1 | 0.72 | 83.1 | 0.22 |
| 6 | 26.5 | 0.68 | 88.2 | 0.20 |
| 7 | 31.2 | 0.58 | | |
| 8 | 32.1 | 0.56 | | |

In this example, on treating the fixed catalyst, as used eight times over, at 200° C. for 10 hours under reduced pressure, the catalyst recovered almost the same performance as that of the 1st use. While in the comparative example, the catalyst used six times over showed no recovery effect even by the same treatment.

What is claimed is:

1. A fixed catalyst for the isomerization of quadricyclanes to norbornadienes which is obtained by dipping an inorganic carrier selected from the group consisting of activated alumina, silica gel, and kaolin, into an aqueous solution of polyamine sulfone, comprising a repeating unit represented by the formula:

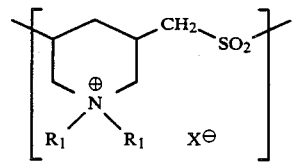

wherein $R_1$ represents a $C_{1-3}$ alkyl and X represents a halogen atom, to be impregnated therewith and drying to form a modified inorganic carrier; dipping the formed modified inorganic carrier into an organic solvent having dissolved therein a porphyrin Co(II) complex represented by the formula:

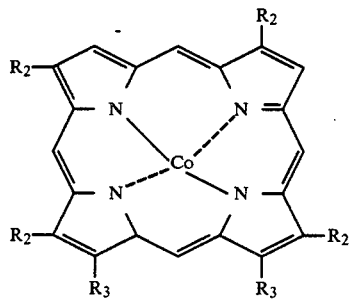

wherein $R_1$ is defined above, $R_2$ represents a $C_{1-3}$ alkyl group and $R_3$ represents a group of the formula —$C_nH_{2n}$—COOH, wherein n is 1 to 4, to be impregnated therewith; and removing the organic solvent whereby the prophyrin Co(II) complex is absorbed and fixed on said modified inorganic carrier.

* * * * *